United States Patent [19]

Santini

[11] 4,366,431
[45] Dec. 28, 1982

[54] BATTERY GASSING DETECTOR

[75] Inventor: John Santini, Centerreach, N.Y.

[73] Assignee: EHV Systems, Inc., Setauket, N.Y.

[21] Appl. No.: 212,601

[22] Filed: Dec. 3, 1980

[51] Int. Cl.³ ........................ H02J 7/04; G01N 13/00; G01N 21/00; G01N 21/47

[52] U.S. Cl. .......................................... 320/46; 73/19; 73/DIG. 11; 250/574; 320/48; 324/432

[58] Field of Search ...................... 320/46, 48, 39, 40, 320/2; 340/636; 324/432, 433; 429/4, 7, 91–93, 121; 356/130; 250/574, 577, 215; 73/17 A, 19, DIG. 11

[56] References Cited

U.S. PATENT DOCUMENTS 3,479,859 11/1969 Hager ................................. 73/17 A
4,240,747 12/1980 Harmer ............................. 320/48 X

FOREIGN PATENT DOCUMENTS 2728310 4/1978 Fed. Rep. of Germany ...... 324/432

Primary Examiner—R. J. Hickey
Attorney, Agent, or Firm—Michael F. Brown; Ralph R. Barnard

[57] ABSTRACT

A gassing detector for use in modifying the charge rate in charging circuits for liquid electrolyte secondary cells. A light is reflected from the surface of the electrolyte into a photodetector. A discriminator circuit distinguishes the pulses in the photodetector output characteristic of the rippling caused by gassing of the cell and produces a signal to cause the charger to reduce the charge rate.

11 Claims, 4 Drawing Figures

BATTERY GASSING DETECTOR

REFERENCE TO DISCLOSURE DOCUMENT

This application was the subject, in part, of Disclosure Document Ser. No. 087917, filed Feb. 4, 1980.

BACKGROUND OF THE INVENTION

This invention pertains to methods and apparatus for determining the state of charge of a secondary battery for the purpose of adjusting the charging rate thereof. More specifically, the invention pertains to methods and apparatus for determining the "gassing point", that is, that charge state at which the electrolyte of the cell begins to break down into gas bubbles.

It has long been known that when attempting to fast-charge secondary cells with fluid electrolytes, such as the common lead-acid storage battery, the cell is capable of accepting high charging currents only until approximately 80–90% charged. At that point the additional energy put into the battery is largely used to break down the electrolyte into hydrogen and oxygen gas, rather than being stored as chemical energy. The charging rate must then be reduced, lest damage occur to the cell through overheating, "boiling" away of the water part of the electrolyte (with a resulting harmful increase in acid concentration), or corrosion of the plates through excessive gassing causing a loosening of the active material.

Many methods have been used to detect this "gassing point" indirectly. Most common are those which sense cell voltage and/or charging current (see, i.e. Van Beek, U.S. Pat. Nos. 4,217,533; Hess, 4,207,513; Scott 4,152,635; Lavell 4,052,656; Clayton 3,660,748; and others). Other indirect methods include use of a timed charger (Hase 3,848,173; Saslow 3,178,629; Buckholder 2,670,039), temperature detectors (Brown 4,061,956; Guelpa 2,666,883), or watt-hour or Coulometers (Sarbacher 3,889,170; Wilson 3,421,067; and many others). All of these indirect methods will, through their indirect nature, tend to approximate the proper charge rate at best. The actual gassing point will vary in response to battery temperature especially, but also to electrolyte condition, age and composition of the cell, and many other factors. To even approximate the proper charge rate an indirect sensing charger must be matched to a specific battery, and even then cannot directly and reliably compensate for environment and age factors.

In some charger designs the charge rate is tied to the specific gravity of the electrolyte by placing a hygrometer in the electrolyte and having the movement of the float interrupt a photoelectric control light beam (Knight U.S. Pat. No. 2,310,700 and others). This method has the same drawbacks as the other indirect methods, and also requires modification of the cell and addition of a potentially fragile external test column.

Direct gassing detectors have most commonly tended to respond to gas pressure in the cell (i.e. Ebbert U.S. Pat. Nos. 3,652,915; Hanson 2,118,558; and others). These have tended to be less than completely successful due to the effects of battery cell volume, temperature, and the small volume of gas produced.

Other more exotic schemes involving recombination of water on a catalytic agent (Zollner, German Pat. No. 28.08.76-DT-638899), injection of ionized gasses (Genin U.S. Pat. Nos. 2,514,235), changes in the velocity of sound (Molyneux 3,798,528), or addition of a third electrode to the battery (Duddy 3,901,729 and current production Yuasa batteries) have been tried as well. All of these systems require sealing and/or otherwise modifying the cell, or addition of complicated, possibly fragile, apparatus to the battery, often involving substances which must be replaced periodically.

Thus, it is an object of this invention to provide an improved method for detecting bubbling on the surface of a liquid, for example the bubbling characteristic of the "gassing point" of a battery under charge.

It is a further object of the invention to provide an improved battery gassing detector for use with secondary battery charging circuits.

Further, it is an object of this invention to provide a simple, rugged, means of directly detecting when a cell has reached the gassing point which can be used with any liquid electrolyte battery without sealing or modifying the battery, and without externally handling the electrolyte or gas.

The direct photoelectric detection of bubbling on the surface of a liquid represents a novel and distinct advance in the art. In battery charger applications, it represents an advance over time, voltage, and other indirect methods because it detects gassing directly, thus the effects of variables such as pressure, temperature and battery condition become unimportant. The photoelectric detector disclosed by this application represents an advance over any of the methods requiring modification of the cell because it can be employed by the designer in a charging system for any liquid-electrolyte battery without the expense and complication of requiring the battery manufacturer to supply modified cells. Moreover, it can be used with existing cells with no retrofitting of additional electrodes, etc. Unlike the catalytic and third-electrode systems, the detector is not consumed and needs no more maintenance than a simple cleaning when checking electrolyte level. It represents an advance over any of the systems which pipe electrolyte or gas outside the battery case in that it requires no external pipes or attachments which are a source of problems in the rugged environment of a motor vehicle.

Other advantages will become apparent upon further examination of the disclosure.

SUMMARY OF THE INVENTION

The present invention relates to methods and apparatus for detecting bubbling on the surface of a liquid, which may be applied to the detection of gassing of the electrolyte during charging of a liquid electrolyte secondary cell to enable modification of the charging rate. The detection is performed by photoelectrically detecting the bubbling on the surface of the electrolyte. More specifically, the detection is accomplished by shining a light source on the surface of the electrolyte and detecting the reflected light in a photodetector. Momentary surface disturbances are ignored, and the genuine ripples produced by gassing are detected, by electronic processing of the photodetector output.

BRIEF DESCRIPTION OF THE DRAWINGS

The invention will be more fully understood from the following detailed description, in connection with the accompanying drawings, in which:

DESCRIPTION OF THE INVENTION: FIGS. 1 and 2

FIG. 1 shows an over-all block diagram of the invention. In a cell (1) of a conventional secondary battery are located the plates (2) immersed in a liquid electrolyte (3). Leads (4) connect the battery to a charger (5) of conventional design, with a plurality of charging rates, controllable through an external input.

Figure 1:
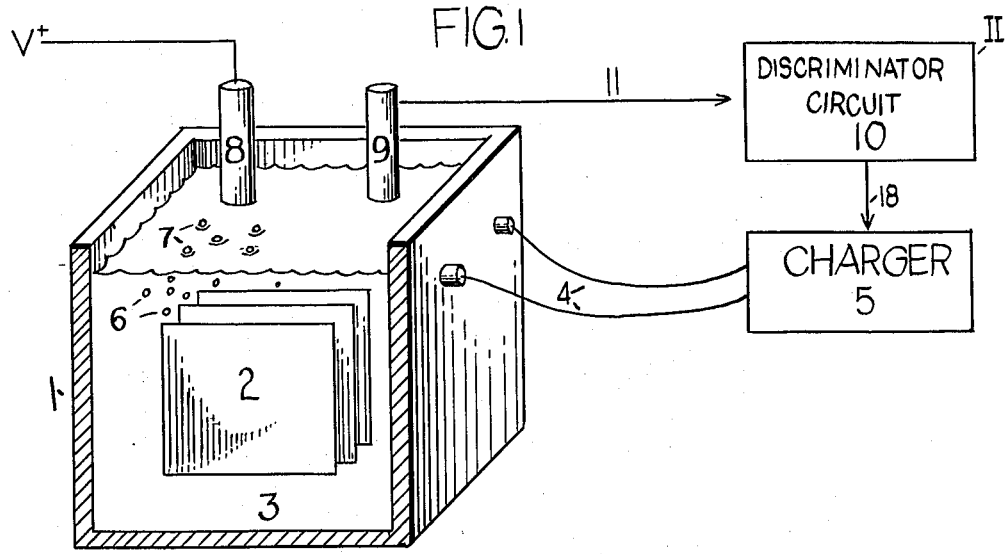
FIG. 1 shows a drawing of the over-all invention.

In the battery, located above the electrolyte surface, and thus not in contact with or penetrating the surface, is a light source (8) and photodetector (9). As used herein, the term "Electrolyte Surface" means the upper surface of the liquid, that is, the interface between the liquid and the air or gas volume above.

Light from the light source (8) shines on the surface of the electrolyte. When still, the surface reflects a constant amount of light into a photodetector (9). When the battery has charged to the gassing point bubbles (6) rise to the surface of the electrolyte, causing ripples (7). The ripples create a changing signal in the photodetector. The output of the photodetector (11) is fed into a discriminator circuit (10), detailed in FIG. 2, which distinguishes between slow, momentary, or erratic fluctuations and the regular pulses caused by the bursting bubbles of gassing. The output of the discriminator (18) is fed into the charger (5) causing it to change charging rate.

Figure 2:
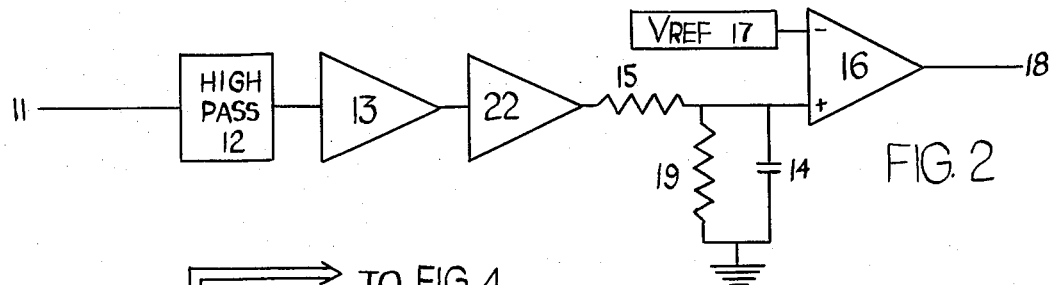
FIG. 2 is a diagram of the discriminator circuit.

FIG. 2 shows a diagram of the discriminator circuit. Conventional details of amplifier construction, power supply connections, and the like have been omitted for clarity. The signal (11) from the photodetector (9) passes through a high-pass network (12) which filters out the constant signals, indicative of a still surface, and slow changes in the photodetector output. The filtered signal is amplified by a conventional amplifier (13) and charges a capacitor (14) through a current amplifier (22) and a charge-rate regulator (here resistor (15)). The capacitor and resistor form an integrator which ensures that several ripples must be detected within a short time in order to raise the integrator output (capacitor charge voltage) to the detection point. Resistor (19) bleeds off the capacitor charge at a slow rate to avoid buildup due to widely spaced random pulses. The integrator output is compared in a voltage comparator (16) with a detection point set by a voltage source (17). When the capacitor charge exceeds the detection point the output of the comparator (18) changes state, and signals the charger (5) to reduce the charge rate.

Figure 3:
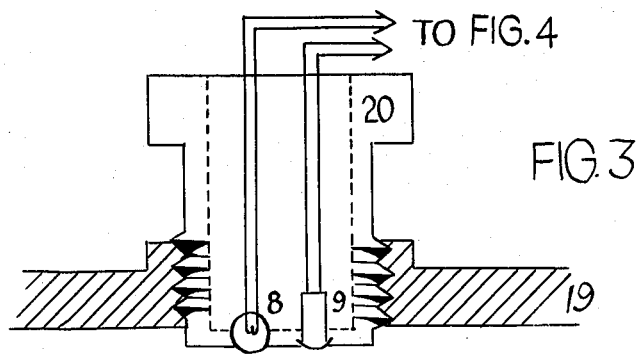
FIG. 3 shows one feature of the preferred embodiment of the invention, in which the light source and photodetector are mounted within the filler cap of the cell.
Figure 4:
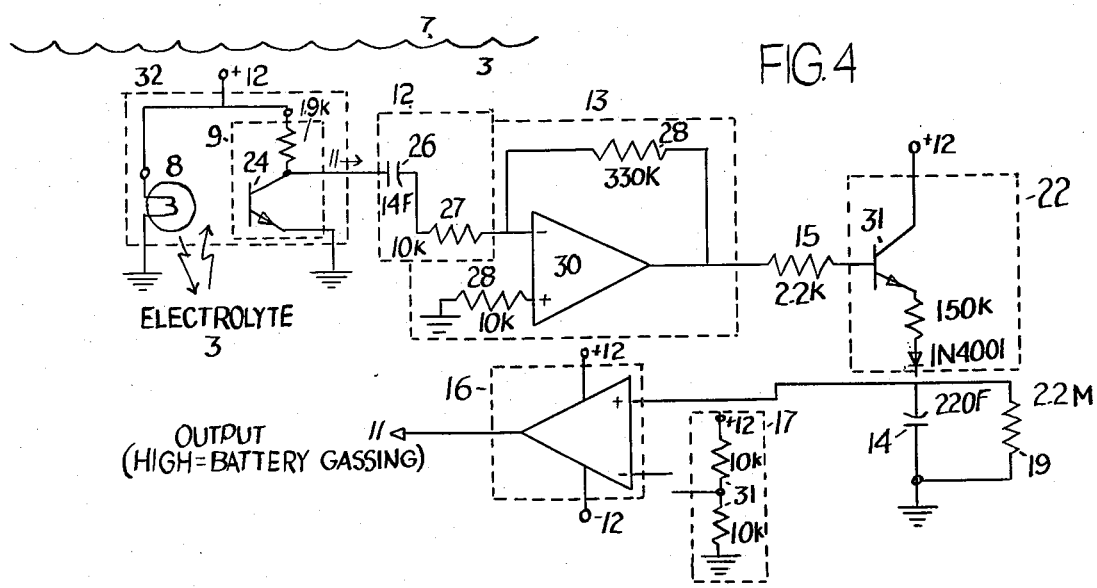
FIG. 4 is a detailed schematic of the preferred embodiment, with the basic sections of FIG. II indicated by dashed lines.

DETAILED DESCRIPTION OF THE PREFERRED EMBODIMENT: FIGS. 3 and 4

In the preferred embodiment of the invention (shown in a side cut-away view in FIG. 3) a small light bulb or LED (8) and a photodetector (9) are mounted within, or affixed to the bottom of, the filler cap (20) which fits into the top surface of a conventional storage battery (19). The photodetector is preferably a phototransistor such as a Texas Instruments TIL81, or similar device of appropriate size and characteristics. The optical surfaces (i.e. photodetector light sensitive area, light source output) are directed downward toward the surface of the electrolyte but do not contact or penetrate the surface.

Referring to FIG. 4, the phototransistor output voltage (11) is fed through a high-pass network (12) comprising a series circuit of a 1 microfarad capacitor (26) and a 10 Kilohm resistor (27). This network filters out the constant level created by reflection from a still surface and slower pulses and passes the relatively fast (about 1 millisecond) pulses caused by genuine bubbles. The filter output is fed to the input of an operational amplifier (30) such as, for example, one section of an LM 324, or any other similar op amp. The gain of the amplifier stage is set by resistors (28). The amplified signal is used to operate a current amplifier (22) comprising a transistor (31), resistor and diode. The transistor could be any small type such as a 2N2222. The current amplifier output charges a 22 microfarad capacitor (14). The 2.2 Kilohm current-limit resistor limits the charging current so that several ripples must be detected in a relatively short time (some 5 to 40 seconds) to charge capacitor (14) to the detection point. A 2.2 Megohm resistor (19) slowly discharges the capacitor (in approximately 40 seconds) so that the voltage rise caused by only occasional ripples will not accumulate and cause false triggering. If sufficient signals are received to raise the voltage on capacitor (14) above the threshold set by the resistive voltage divider (17) the normally low output (11) of the voltage comparator (16), which can be an operational amplifier such as one section of an LM324 or the like, will go to a "high" logic state indicating the gassing point has been reached and the charging current must be reduced.

It should be noted that the illustrated embodiments have been described largely with respect to battery chargers. However, those skilled in the art will recognize that the principles herein described and illustrated are applicable to a wide variety of applications in which detection of bubbling is necessary.

Accordingly, it is to be understood that the embodiments of the invention herein described are merely illustrative of the application of the principles of the invention. Reference herein to details of the illustrated embodiments are not intended to limit the scope of the claims which themselves recite those features regarded as essential to the invention.

I claim:

1. An apparatus for detecting bubbling on the surface of a liquid, comprising:

a. light emitting means for directing a light at the surface of the liquid;

b. photodetector means for generating a signal responsive to the light reflecting from the surface of the liquid, having an input for the reflected light and an output responsive to the amount of liquid detected;

c. said light emitting means and said photodetector means being located above the surface of the liquid;

d. discriminator means for distinguishing signals caused by bubbling having an input connected to the photodetector means output and having an output responsive to the detection of bubbling in the liquid.

2. The apparatus of claim 1 in which the discriminator means comprises:

a. an input for accepting the photodetector output signal;

b. filter means for eliminating signals indicative of steady-state conditions or slow change, having an input connected to the input means, and an output for the faster pulses;

c. integrator means for accumulating pulses, having an input connected to the output of the filter means and an output proportional to the number of pulses received;

d. a reference voltage means having an output equal to that value of the integrator output which is indicative of sufficient pulses to constitute bubbling;

e. Comparator means for comparing the output of the integrator means with the output of the reference means, having inputs connected to the integrator and reference means, and an output which changes state when the input from the integrator is larger than that from the reference.

3. The apparatus of claim 1 in which the liquid is the electrolyte of a battery.

4. The apparatus of claim 3 in which the discriminator means output is used to modify the charging rate of a battery charger.

5. A battery gassing detector for determining the state of charge of a liquid electrolyte secondary battery, comprising:

a. means for illuminating the surface of the liquid electrolyte, located above the surface having a light output shining on the surface;

b. photodetector means having a light sensitive input and a signal output, located above the surface such that the light from the illuminating means is reflected from the surface onto the light sensitive input of the photodetector;

c. discriminator means having an input connected to the signal output of the photodetector and an output responsive to the detection of a pattern of pulses in the output of the photodetector which is characteristic of bubbling.

6. The detector of claim 6 in which the discriminator means comprises:

a. high-pass filter means connected to the signal input for attenuating pulses of duration longer than 1 millisecond, having an output for those pulses of 1 millisecond or shorter duration;

b. current amplifier means having an input connected to the output of the high-pass filter, and an output current proportional to the input;

c. a capacitor charged by the output of the current amplifier;

d. a voltage reference for determining the state of capacitor charge which represents gassing;

e. voltage comparator means with inputs connected to the capacitor and the reference, and an output responsive to the difference between the reference and the capacitor voltages, which reference is the output of the discriminator circuit.

7. The detector of claim 5 in which the battery has a plurality of filler cap means for checking and maintaining the liquid level, and in which the photodetector and light source are located in at least one of the filler caps.

8. The detector of claim 5 in which the output of the discriminator means is used to modify the charging rate of a charger connected to the battery.

9. The method of detecting bubbling on the surface of a liquid comprising the steps of:

a. shining a light on the surface of the liquid from a position above said surface;

b. measuring the reflected light from a position above the surface of the liquid;

c. distinguishing the reflected light characteristic of bubbling from that of a still surface by the steps of filtering out all slow changes in measured light, accumulating the faster changes, and comparing the accumulated charge with a preset level indicative of bubbling.

10. The method of claim 9 in which the liquid is the electrolyte of a battery.

11. The method of claim 10 further comprising the step of modifying the charge rate of the battery responsive to the detection of bubbling.

* * * * *